US00PP35254P3

(12) United States Plant Patent
Shimoda et al.

(10) Patent No.: US PP35,254 P3
(45) Date of Patent: Jul. 4, 2023

(54) MAITAKE MUSHROOM NAMED 'YUKIGUNIMAI 14GO'

(50) Latin Name: *Grifola frondosa*
Varietal Denomination: YUKIGUNIMAI 14GO

(71) Applicant: Yukiguni Maitake Co., Ltd., Minamiuonuma (JP)

(72) Inventors: Takafumi Shimoda, Minamiuonuma (JP); Junye Jia, Minamiuonuma (JP); Takuto Shimizu, Minamiuonuma (JP); Masayuki Sato, Minamiuonuma (JP)

(73) Assignee: Yukiguni Maitake Co., Ltd., Minamiuonuma (JP)

( * ) Notice: Subject to any disclaimer, the term of this patent is extended or adjusted under 35 U.S.C. 154(b) by 0 days.

(21) Appl. No.: 17/803,131

(22) Filed: Feb. 28, 2022

(65) Prior Publication Data

US 2023/0103285 P1 Mar. 30, 2023

(30) Foreign Application Priority Data

Sep. 24, 2021 (JP) ..... 2021-155669
Sep. 28, 2021 (JP) ..... 35739

(51) Int. Cl.
*A01H 15/00* (2006.01)

(52) U.S. Cl.
USPC ..... Plt./394
CPC ..... *A01H 15/00* (2013.01)

(58) Field of Classification Search
USPC ..... Plt./394
CPC ..... A01H 15/00
See application file for complete search history.

(56) References Cited

PUBLICATIONS

Nobuhisa Kawaguchi, et al., "Genetic Analyses of Causal Genes of albinism (white fruiting body) in *Grifola frondosa*," *J. Wood Sci.*, (2019) 65:32, pp. 1-9.
Nishibori et al., "Maitake", *Seibutsu-kogaku* (*Bioengineering*), vol. 92, No. 10, pp. 572-575 (2014)—(with English translation).

*Primary Examiner* — Anne Marie Grunberg
(74) *Attorney, Agent, or Firm* — Oblon, McClelland, Maier & Neustadt, L.L.P.

(57) ABSTRACT

The present invention relates to a new and distinct White Maitake variety named 'YUKIGUNIMAI 14GO', which is characterized by: (1) there is no color unevenness throughout the caps of the fruit body, and it has a homogeneous white color; (2) it has a remarkably low incidence of the caps to be colored in the fruit body; and (3) it does not become colored even under black light irradiation including ultraviolet light.

21 Drawing Sheets

Latin name: *Grifola frondosa.*
Variety denomination: 'YUKIGUNIMAI 14GO'.

CROSS-REFERENCE TO RELATED APPLICATION

This application claims priority of Japanese Patent Application No. 2021-155669 filed on Sep. 24, 2021, and Japanese Plant Variety Registration Application No. 35739 filed on Sep. 28, 2021, which are incorporated by reference herein as if set forth in its entirety.

BACKGROUND OF THE INVENTION

Maitake is a wood-decaying fungus belonging to the order Polyporales, the family Grifolaceae, the genus *Grifola*, which is distributed in Asia, Europe, North America in the temperate north, and Australia. In Japan, it occurs in the ridge of deep mountains in early autumn, and in the roots of trees emerging on the surface of old large trees, such as Japanese oak, oak, chestnut (Tohoku region), and chinquapin (west Japan), where the weather is well-ventilated and relatively daily. Maitake mushroom (*Grifola frondosa*) and White Maitake mushroom (*Grifola albicans*) are known, but white mushroom has been known to be the same species as Maitake (for example, "Shin Bunrui Kinoko Zukan (new taxonomic mushroom cartoon)", page 356, HOKURYUKAN, 2021) and is described herein as the same species (all names are denoted as *Grifola frondosa*). Maitake and White Maitake mushrooms are edible, and artificial cultivation methods have also been established. Characteristics of the fruit body of Maitake are as follows: the stipe and cap (so-called mushroom type) of many edible mushrooms produced in artificial cultivation such as Enokitake (*Flammulina velutipes*) and Bunashimeji (*Hypsizygus marmoreus*) can be clearly distinguished, whereas Maitake has many overlapping light black-brown and dark brown-brown caps that cannot be clearly distinguished between the stalk and cap parts to form large fruit body (so-called Sarunokoshikake type) (Seibutsu-kogaku (Bioengineering), Vol.92, No.10, pp.572-575, 2014).

White Maitake mushroom is considered to be edible similarly to Maitake, but unlike Maitake, it is characterized by white to cream colors and does not have the color of Maitake on its boiling, etc., so it is valuable for cooking, etc. that emphasizes color. As the function of Maitake, immunostimulatory activity, antioxidant activity, antiviral activity, etc. have been reported (e.g., JP 2020-002052 A, and Seibutsu-kogaku (Bioengineering), Vol.92, No.10, pp.572-575, 2014), and White Maitake is expected to have comparable function.

Because some of caps on the fruit body of White Maitake mushrooms may be brown in color, the commodity value as White Maitake mushrooms is lost or a process in which the colored parts are removed when commercialized is necessary. Therefore, White Maitake which is difficult to color and its cultivation method have been needed.

SUMMARY OF THE INVENTION

We have succeeded in obtaining a novel White Maitake variety having characteristics that there is no color unevenness throughout the caps of the fruit body, a homogeneous white color, and a remarkably low incidence of caps to be colored in the fruit body. We have also found that this White Maitake variety has the characteristics that it does not become colored even under black light irradiation including ultraviolet light. The White Maitake variety has high commercial value, and also does not require a step of removing a colored portion at the time of commercialization, and has commercial utility.

This novel and distinct variety of mushroom is identified as 'YUKIGUNIMAI 14GO'.

BRIEF DESCRIPTION OF THE DRAWINGS

This novel mushroom variety is illustrated by the accompanying color photographs, depicting defining characteristics of the mushroom by the best possible color photography.

DETAILED DESRIPTION OF THE INVENTION

Figure 1:
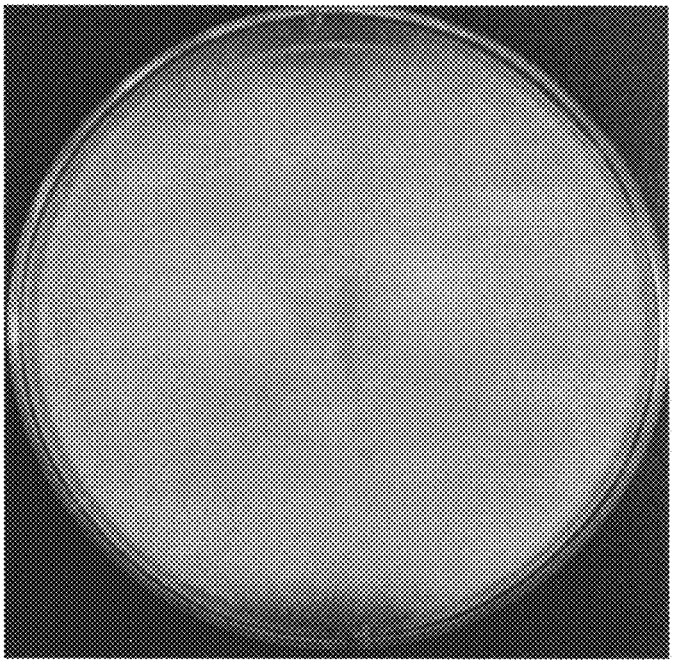
FIG. 1 is a photograph showing top view of dual culture in which a pair of 'YUKIGUNIMAI 14GO' strains of the invention are placed alongside.

The present invention relates to a new and distinct White Maitake variety named 'YUKIGUNIMAI 14GO', which is characterized by:

(1) there is no color unevenness throughout the caps of the fruit body, and it has a homogeneous white color;
(2) it has a remarkably low incidence of the caps to be colored in the fruit body; and
(3) it does not become colored even under black light irradiation including ultraviolet light.

Hereinafter, the invention is explained by using a standard variety 'MORI 51GO' and a similar variety 'MORI 60GO' (Mori & Company) as comparative varieties.

A. BREEDING PROCESS HISTORY AND PROCEDURE

'YUKIGUNIMAI 14GO' was obtained by crossing of a white mutant strain AYM86 derived from YUKIGUNIMAI 10GO and a white mutant strain C3843W derived from YUKIGUNIMAI 12GO:

1.: White mutant strain of YUKIGUNIMAI 10GO (AYM86)
2.: White mutant strain of YUKIGUNIMAI 12GO (C3843W)

The strains 'YUKIGUNIMAI 10GO' and 'YUKIGUNIMAI 12GO' were all developed and duly registered by the assignee's company in Japan.

Spores were isolated from fruit body of the mutant strains, and then monokaryotic hypha derived from those spores were crossed reciprocally on November 2016 to produce and select mating strains. The selected mating strains were cultivated in 500 cc bottles filled with broad-leaved sawdust and nutrient-supplemented medium, and several dozens of mating strains in which white maitake fruit body arose were selected. After April 2017, the selected mating strains were further selected through similar culture medium and pouch cultivation using a maitake cultivation bag. A new variety with excellent cultivation and morphological characteristics ('YUKIGUNIMAI 14GO'), in which the whole caps of the fruit body did not differ in color and showed homogeneous white color, was selected. It was confirmed that the characteristics were stable, and the cultivation was completed.

(Information Pertaining to Where Asexual Reproduction Occurred)

YUKIGUNIMAI 14GO is Maitake mushroom developed and discovered by the Research and Development Department of Yukiguni Maitake Co., Ltd. The mycelium of YUKIGUNIMAI 14GO was obtained by crossbreeding mycelia on potato dextrose agar medium and cultured in an incubation room at 25° C. A portion of the mycelium was inoculated onto an oga medium and grown in a room with controlled temperature, humidity, and carbon dioxide concentration to obtain fruiting bodies. A portion of the obtained fruiting bodies was cut off and inoculated onto potato dextrose agar medium, and the mycelium was again obtained by cultivation in an incubation room at a temperature of 25° C. Asexual growth of the mycelium was then performed in the same way by inoculating a portion of the mycelium into potato dextrose medium and culturing at 25° C. Asexual reproduction occurred in Niigata, Japan.

B. CHARACTERISTICS OF 'YUKIGUNIMAI 14GO'

(1) Taxonomic characteristics: Basidiomycetes, the genus Maitake (*Grifola*), Maitake (*Grifola frondosa*).

By dual culture, a method for determining different genetic properties on agar, 'YUKIGUNIMAI 14GO' was determined to be genetically different from other White Maitake varieties and to be a new variety (see, (2) below).

Examples of Culture Conditions:

Potato dextrose agar (PDA).

Figure 2:
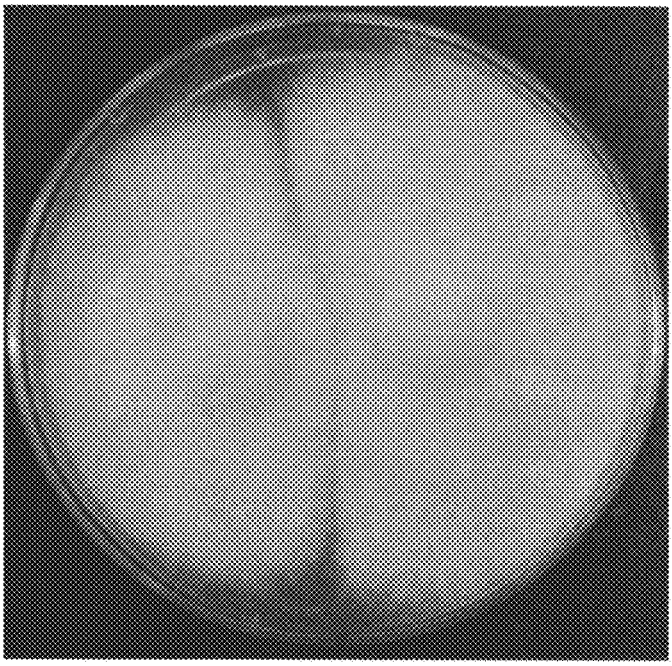
FIG. 2 is a photograph showing top view of dual culture in which a pair of 'YUKIGUNIMAI 14GO' strain of the invention (right) and control strain 'MORI 60GO' (left) are placed alongside.
Figure 3:
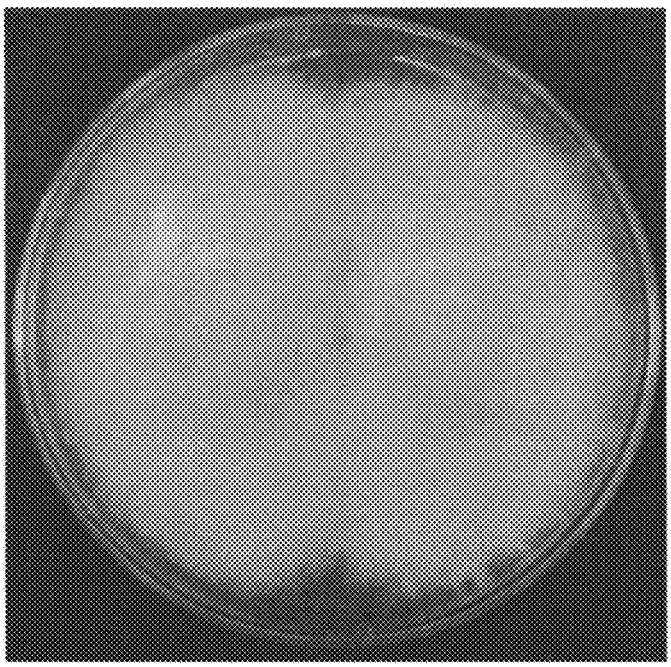
FIG. 3 is a photograph showing top view of dual culture in which a pair of control 'MORI 60GO' strains are placed alongside.

Potato extract 0.4% w/v, glucose 2% w/v, agar 1.5% w/v, pH 5.6, sterile, 121° C., 15 min Culture temperature: 25° C.; Period: 14-28 days; Static culture (2) Genetic Characteristics:

It is well known that zone line is formed occurs between both colonies when mycelia of different mushrooms are subjected to dual culture on agar. Therefore, YUKIGUNIMAI 14GO and MORI M60GO and four commercially available White Maitake varieties were subjected to dual culture on potato dextrose agar at 25° C. for 28 days to observe the presence or absence of zone line. Petri dishes with a diameter of 9 cm were used to prepare the culture medium. The results are shown in FIGS. 1-3 and summarized in Table 1-1. FIG. 1 is a photograph showing top view of dual culture in which a pair of 'YUKIGUNIMAI 14GO' strains of the invention are placed alongside. FIG. 2 is a photograph showing top view of dual culture in which a pair of 'YUKIGUNIMAI 14GO' strain of the invention (right) and control strain 'MORI 60GO' (left) are placed alongside. FIG. 3 is a photograph showing top view of dual culture in which a pair of control 'MORI 60GO' strains are placed alongside. In Table 1-1, between colonies, there was a zone line (+) if it formed a zone line, and no zone line (−) if it did not form a zone line.

TABLE 1-1

Genetic differences due to dual cultures

| Pair | MORI M60GO | Company A Variety 1 | Company A Variety 2 | Company B Variety | Company C Variety | YUKIGUNIMAI 14GO |
|---|---|---|---|---|---|---|
| YUKIGUNIMAI 14GO | + | + | + | + | + | − |

'YUKIGUNIMAI 14GO' was found to be genetically distinct from MORI M60GO or other white maitake varieties because it showed zone lines with all MORI M60GO or other company's white maitake varieties.

Figure 15:
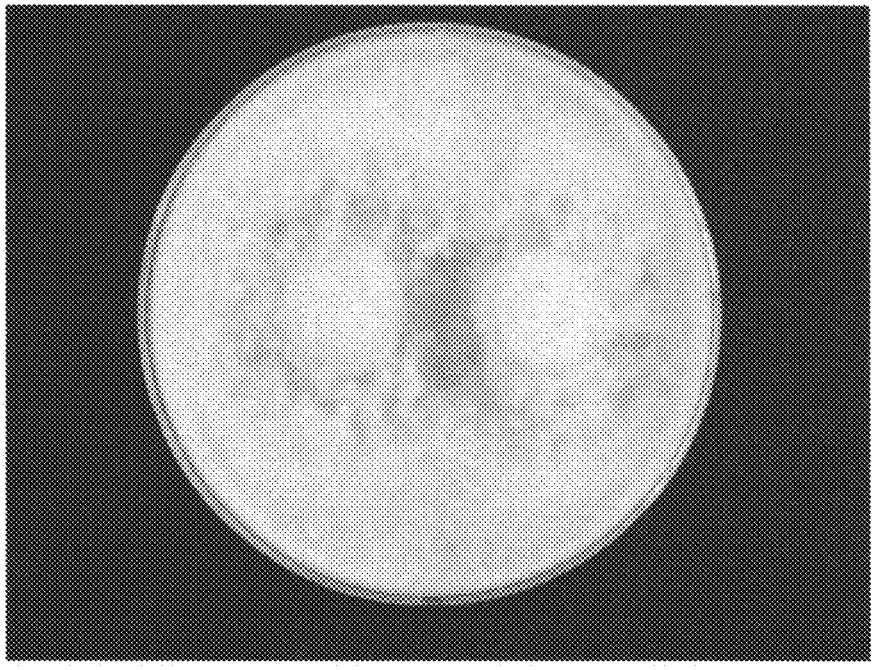
FIG. 15 is a photograph showing top view of dual culture in which a pair of 'YUKIGUNIMAI 14GO' strains of the invention are placed alongside.
Figure 16:
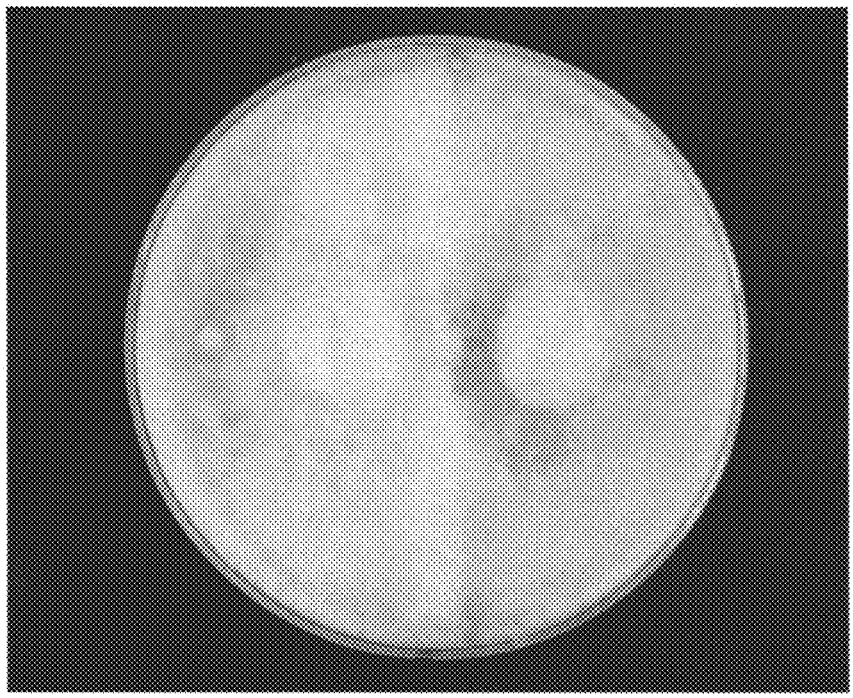
FIG. 16 is a photograph showing top view of dual culture in which a pair of 'YUKIGUNIMAI 14GO' strain of the invention (left) and 'AYM86' (left) are placed alongside.
Figure 17:
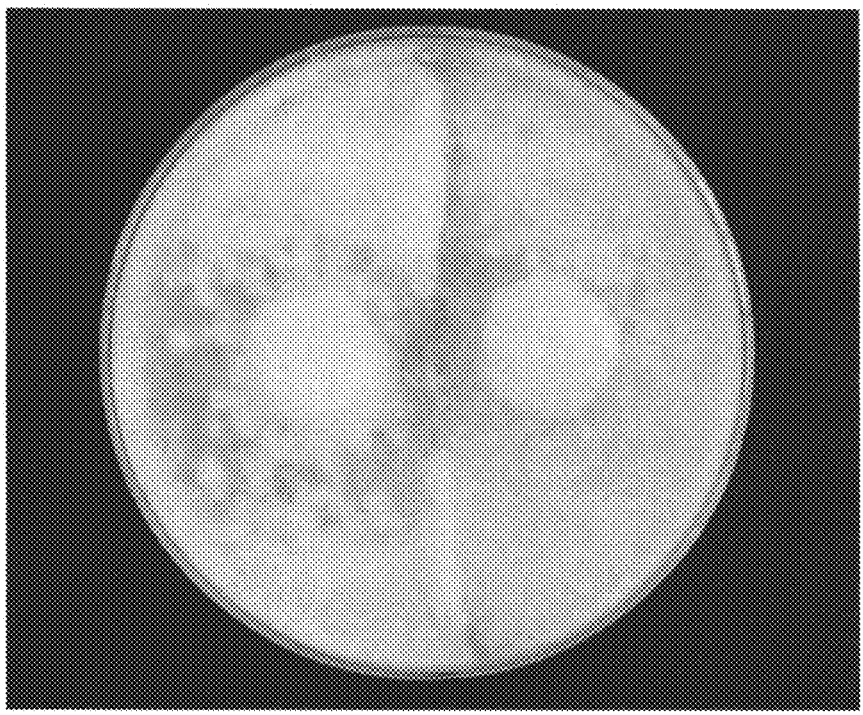
FIG. 17 is a photograph showing top view of dual culture in which a pair of 'YUKIGUNIMAI 14GO' strain of the invention (left) and 'C3843W' (left) are placed alongside.

YUKIGUNIMAI 14GO and their parents (AYM86, C3843W) were subjected to dual culture on potato dextrose agar at 25° C. for 28 days to observe the presence or absence of zone line. Petri dishes with a diameter of 9 cm were used to prepare the culture medium. The results are shown in FIGS. 15-17 and summarized in Table 1-2. FIG. 15 is a photograph showing top view of dual culture in which a pair of 'YUKIGUNIMAI 14GO' strains of the invention are placed alongside. FIG. 16 is a photograph showing top view of dual culture in which a pair of 'YUKIGUNIMAI 14GO' strain of the invention (left) and 'AYM86' (left) are placed alongside. FIG. 17 is a photograph showing top view of dual culture in which a pair of 'YUKIGUNIMAI 14GO' strain of the invention (left) and 'C3843W' (left) are placed alongside. In Table 1-2, between colonies, there was a zone line (+) if it formed a zone line, and no zone line (−) if it did not form a zone line.

TABLE 1-2

Genetic differences due to dual cultures

| Pair | AYM86 | C3843W | YUKIGUNIMAI 14GO |
|---|---|---|---|
| YUKIGUNIMAI 14GO | + | + | − |

'YUKIGUNIMAI 14GO' showed zone lines with its parental strains AYM86 and C3843W.

(3) Physiological Characteristics and Morphological Characteristics:

As physiological characteristics when cultured on potato dextrose agar at 25° C. for 14 days, the hyphal density is dense, the degree of development of aerial hyphae is much, and the colony is thick when compared to conventional variety MORI M60GO. In addition, the shape of colony periphery was homogeneous, the tinting of colony surface was absent, and the shape of colony surface was smooth. The optimum temperature for mycelial growth is around 28° C., and the optimum temperature of fruit body development is around 21° C.

Specifically, as Experiment 1, when cultured on potato dextrose agar at 25° C. for 14 days, the hyphal density, development of aerial hyphae, shape of colony periphery, thickness of colony, tinting of colony surface, and shape of colony surface were observed.

As a result, YUKIGUNIMAI 14GO showed that the hyphal density was dense, the development degree of aerial hyphae was much, and the colony was thick when compared to MORI M60GO. In addition, the shape of colony periphery was homogeneous, the tinting of colony surface was absent, and the shape of colony surface was smooth.

As Experiment 2, the optimum temperature for mycelial growth was determined by pre-culturing for 4 days at 23±1° C. on potato dextrose agar for adjusting the hyphae regeneration (about 10 mm in diameter), and then measuring the mycelial growth length after cultivation at 22° C., 24° C., 26° C., 28° C., 30° C., 32° C., and 34° C. for 16 days. It was confirmed that the growth optimum temperature of YUKIGUNIMAI 14GO was around 28° C., which was lower than that of MORI M60GO.

The results are summarized in Table 2.

TABLE 2

Mycological characteristics

| Strain | YUKIGUNIMAI 14GO | MORI M60GO | MORI M51GO | AYM86 | C3843W |
|---|---|---|---|---|---|
| 1: Hyphal density | Dense | Medium | Dense | Dense | Dense |
| 2: Development of aerial hyphae | Much | Medium | Much | Much | Much |

TABLE 2-continued

| Mycological characteristics | | | | | |
|---|---|---|---|---|---|
| Strain | YUKIGUNI-MAI 14GO | MORI M60GO | MORI M51GO | AYM86 | C3843W |
| 3: Shape of colony periphery | Homo-geneous | Homo-geneous | Rough | Rough | Rough |
| 4: Thickness of colony | Thick | Medium | Thick | Thick | Thick |
| 5: Tinting of colony surface | Absent | Absent | Absent | Absent | Absent |
| 6: Shape of colony surface | Smooth | Smooth | Smooth - island form | Smooth | Smooth |
| 7: Optimum temperature for mycelial growth | 28° C. | 30° C. | 28° C. | — | — |

In addition, as Experiment 3, the growth rate at each temperature was determined by pre-culturing for 4 days at 23±1° C. on potato dextrose agar for adjusting the hyphae regeneration (about 10 mm in diameter), and then measuring the mycelial growth length after pre-cultivation at each temperature zone of 10° C., 15° C., 20° C., 25° C., and 30° C. for 10 days. The results are provided in Table 3. Experimental results confirmed that YUKIGUNIMAI 14GO had faster mycelial growth rates at 10° C., 15° C., 20° C., and 30° C. compared with MORI M60GO.

TABLE 3

| Growth rate (mm/day) at each culture temperatures. | | | |
|---|---|---|---|
| Strains | YUKIGUNIMAI 14GO | MORI M60GO | MORI M51GO |
| 8: 10° C. | 1.54 | 1.32 | 1.28 |
| 9: 15° C. | 2.08 | 1.61 | 1.53 |
| 10: 20° C. | 2.60 | 2.29 | 2.44 |
| 11: 25° C. | 2.95 | 3.27 | 3.71 |
| 12: 30° C. | 3.67 | 3.52 | 4.07 |

(4) Cultivation Characteristics and Morphological Characteristics:

The cultivation characteristic test was carried out using a medium in which hardwood sawdust mainly composed of beech wood and corn bran were mixed at a ratio of 75:25 in a dry weight ratio, and the water content was adjusted to about 61%. The cultivation container used was a polypropylene cultivation bag (square shape, 8500 cc, diameter of about 200×120 mm, height of about 440 mm) with a ventilation filter. The cultivation bag was filled with an amount of 2500±50 g per bag and pressed so as to have a medium height of about 15 cm, 2 inoculation holes having a diameter of about 15 mm downward were pored, and the bag was sterilized by autoclaving. After sterile cooling, approximately 20-25 ml of sawdust inoculum was inoculated per bag, and the upper part of the bag was folded and the shape was adjusted so that the filter part was on surface. Cultures were performed at temperatures of 22±1° C., humidity of approximately 70-75% RH, and fluorescent light illumination of 200-500 lux, with primordia formation to complete cultures. The fungal bed after the primordia formation was transferred to the development room with temperature 17±1° C., humidity 90-95% RH, and fluorescent light illumination 500-1500 lux, and stimulated the primordia formation for 10 days, after which the filter part was removed and the development to the fruit body was stimulated. The fruit body was harvested when the generated fruit body was sufficiently developed and the pores on the back of the caps were formed to the extent of 2-3 mm from the edge, and the yield of the fruit body was measured after removing the medium adhering to the base of the fruit body.

The period from inoculation to primordia formation, period to maximum fruiting, and fruit body yield were all examined, and the average was calculated. The cultivation test was repeated three times with at least 18 bags per test plot.

As a morphological characterization of fruit body, the fruit body of three standard strains was selected in each replicate, and a total of nine strains were observed for the properties shown in Table 4-1 and recorded. The colors on the cap surface were identified using The Royal Horticultural Society (R.H.S.) Colour Charts Edition V. For the diameter of fruit body cluster on a bag, the long and short diameters of crosshairs at the center of each fruit body were measured, and the average was calculated. The size and thickness of the caps were measured on a total of more than 120 pieces by selecting 10 pieces with standard formation from each fruit body strain.

Further, the investigation of the optimum temperature for fruit body development was carried out separately from the above cultivation characteristic test. At 15° C., 17° C., 19° C. 21° C., and 23° C., development to fruit body was stimulated, and the temperature at which the period from filter removal to harvest was shortest was set as the optimum temperature for development. The investigation was conducted once with at least 17 bags per test plot.

For comparison of the morphological characterization of fruit body with the parental strains AYM86 and C3843W, hardwood sawdust supplemented with a nutrient mixed with such as wheat bran was used as the medium. The cultivation container was a polypropylene cultivation bag with a ventilation filter, and was sterilized by autoclaving after filling the medium. After cooling, the strain was inoculated with sawdust inoculum, cultivated for 60 days or more to an extent that primordia was sufficiently grown (including stimulation of primordia formation), the filter part was removed and the bag was transferred to the development room with temperature of about 17-20° C. and humidity of 80% RH or more to stimulate development to fruit body.

The cultivation characteristics obtained above are shown in Table 4-1 and Table 4-2.

Compared with MORI M60GO, the yield of YUKIGUNIMAI 14GO increased, the caps were larger, and the days for primordia formation and the period to the peak of harvesting were longer. On the other hand, the diameter of fruit body strain, the shape of caps, periphery, and the shape of vertical section of cap did not differ significantly from MORI M60GO.

MORI M60GO had grayish white (GREYED-WHITE GROUP according to R.H.S. Colour Charts) caps (colored caps) among the caps in about 80% of the fruit body strains harvested. In contrast, the fruit body of YUKIGUNIMAI 14GO had no colored cap, and the whole fruit body was white (R.H.S. Colour Charts: White NN155A-B) without uneven color. Thus, YUKIGUNIMAI 14GO was shown to have the property of stably obtaining white caps.

TABLE 4-1

Cultivation characteristics and Morphological characteristics

| Items of cultivation characteristics | YUKIGUNIMAI 14GO | MORI M60GO | MORI M51GO |
|---|---|---|---|
| 13: Fruiting body diameter (mm) | 161.5 | 160.9 | 166.3 |
| 14: Cap size (mm) | 24.9 | 14.5 | 17.8 |
| 15: Cap thickness (mm) | 1.8 | 2.2 | 2.2 |
| 16: Shape of cap | Flabellate | Flabellate | Flabellate |
| 17: Periphery | None | None | None |
| 18: Observe a shape of vertical section of cap | Horizontal to Downward 45° | Horizontal to Downward 45° | Horizontal |
| 19: Color of the cap surface | White NN155A-B | White/grayish white NN155A-B/156A-D | Dark brown N199A |
| 20: Cap: hardness | Soft to Medium | Medium | Medium |
| 21: Shape of zonate spots on cap surface | None to medial periphery | None to medial periphery | Medial periphery |
| 22: Development part of pore | To the vicinity of stalk | To the vicinity of stalk | To the vicinity of stalk |
| 23: Form of the base of cluster | Thin | Medium to Thick | Medium |
| 24: Formation of mycelial mat of the surface of bag-culture | Much | Medium | Little |
| 25: Tinting of mycelial mat of the surface of bag-culture | Present (narrower colored area than MORI M60GO) | Present | Present |
| 26: Period from inoculation to primordia formation (days) | 49.4 | 45.0 | 45.2 |
| 27: Period from inoculation to harvest (days) | 76.4 | 70.5 | 67.4 |
| 28: Optimum temperature for fruit body development (° C.) | 21 | 21 | 21 |
| 29: Fresh weight of fruit body per 2.5 kg sawdust-based bag-culture (g) | 366.1 | 345.4 | 333.6 |
| 19: Incidence (%) of fruit body with colored cap | 0 | 80 | 100 |

TABLE 4-2

Cultivation characteristics and Morphological characteristics

| Items of cultivation characteristics | YUKIGUNI-MAI 14GO | AYM86 | C3843W |
|---|---|---|---|
| Shape of cap | Flabellate | Flabellate | Spine to Flabellate |
| Notch of cap periphery | Absent | Present to Absent | Present |
| Observe a shape of vertical section of cap | Horizontal to Downward 45° | Horizontal to Downward 45° | Upward to Downward 90° |
| Color of the cap surface | White NN155A-B | White NN155B | White NN155B |
| Shape of zonate spots on cap surface | None to medial periphery | None to medial periphery | None |

TABLE 4-2-continued

Cultivation characteristics and Morphological characteristics

| Items of cultivation characteristics | YUKIGUNI-MAI 14GO | AYM86 | C3843W |
|---|---|---|---|
| Development part of pore | stalk from cap | stalk from cap | stalk from cap |
| Period from inoculation to harvest (days) | 87.6 | 88.6 | 92.1 |
| Fresh weight of fruit body per 2.5 kg sawdust-based bag-culture (g) | 749.0 | 720.3 | 546.6 |
| Incidence (%) of fruit body with colored cap | 0 | 0 | Present of colored spot |

In Table 4-1 and Table 4-2, colored caps were identified according to R.H.S. Colour Charts based on the surface of the caps. Colored caps were defined as those belonging to GREYED-WHITE GROUP or GREY-BROWN GROUP. The values in Table 4-1 and Table 4-2 are the average.

Figure 4:
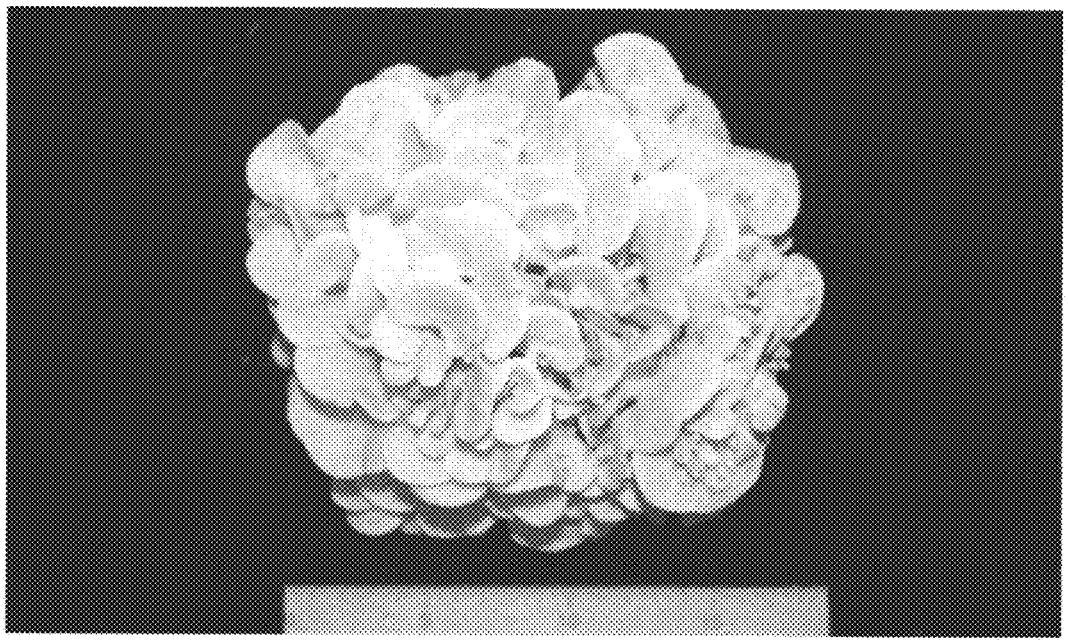
FIG. 4 is a photograph showing top view of a representative strain of YUKIGUNIMAI 14GO.
Figure 5:
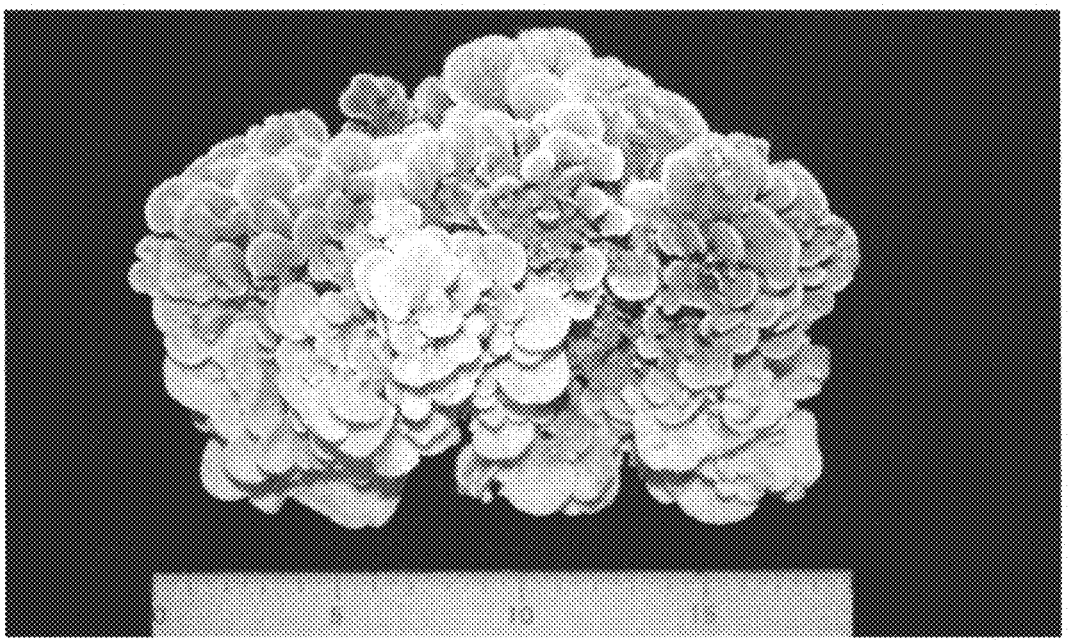
FIG. 5 is a photograph showing top view of a representative strain of MORI M60GO.
Figure 6:
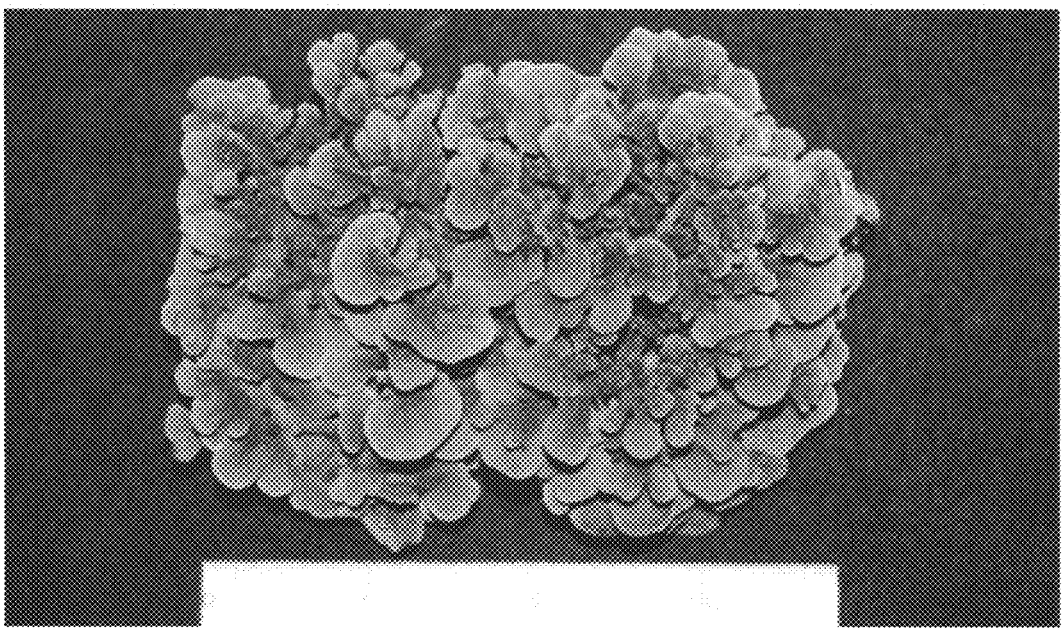
FIG. 6 is a photograph showing top view of a representative strain of MORI M51GO.
Figure 7:
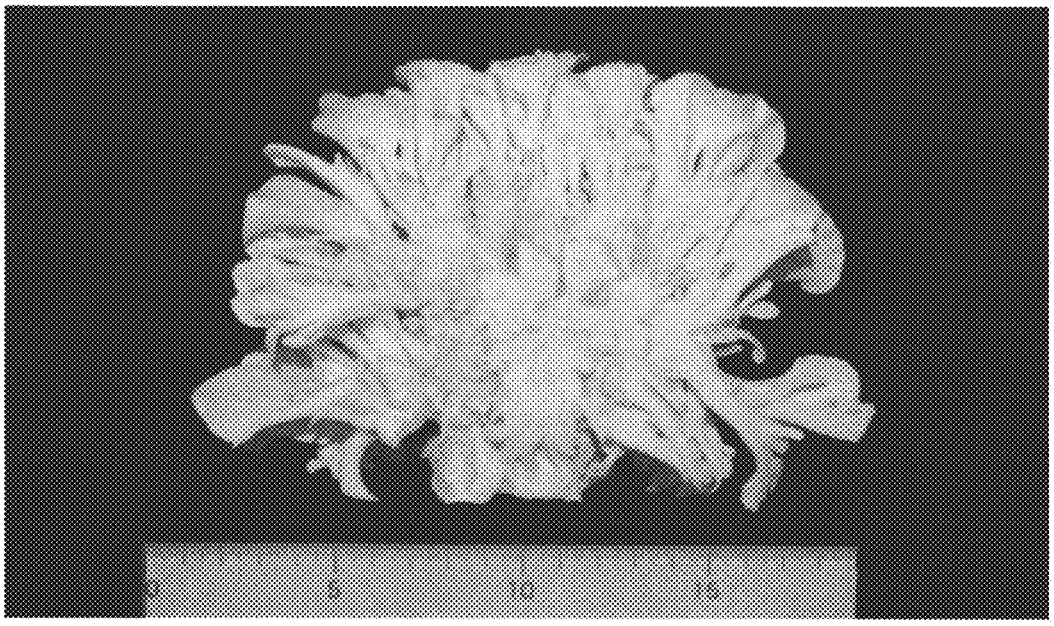
FIG. 7 is a photograph showing cross sectional view of a representative strain of YUKIGUNIMAI 14GO.
Figure 8:
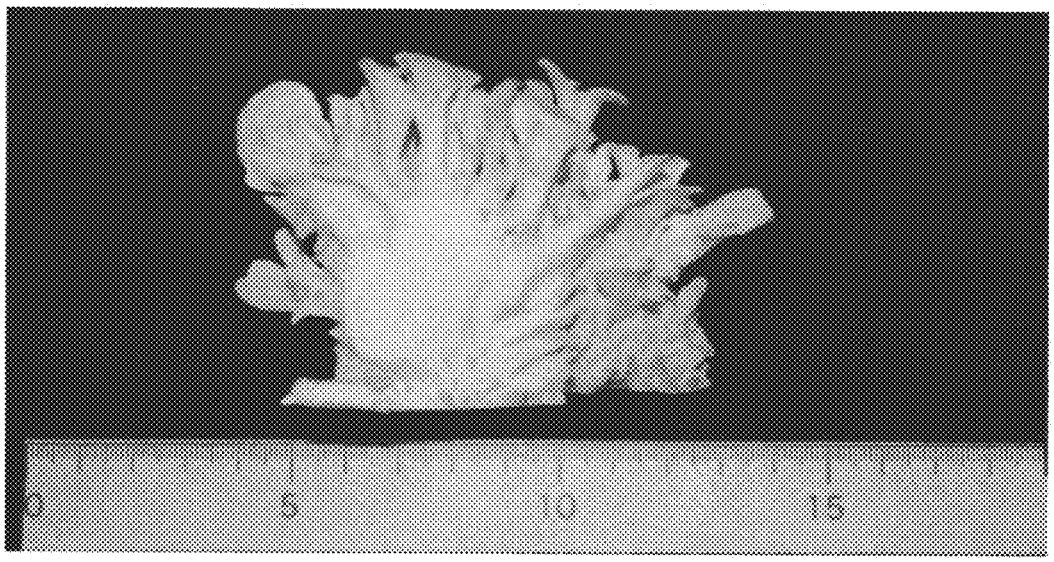
FIG. 8 is a photograph showing cross sectional view of a representative strain of MORI M60GO.
Figure 9:
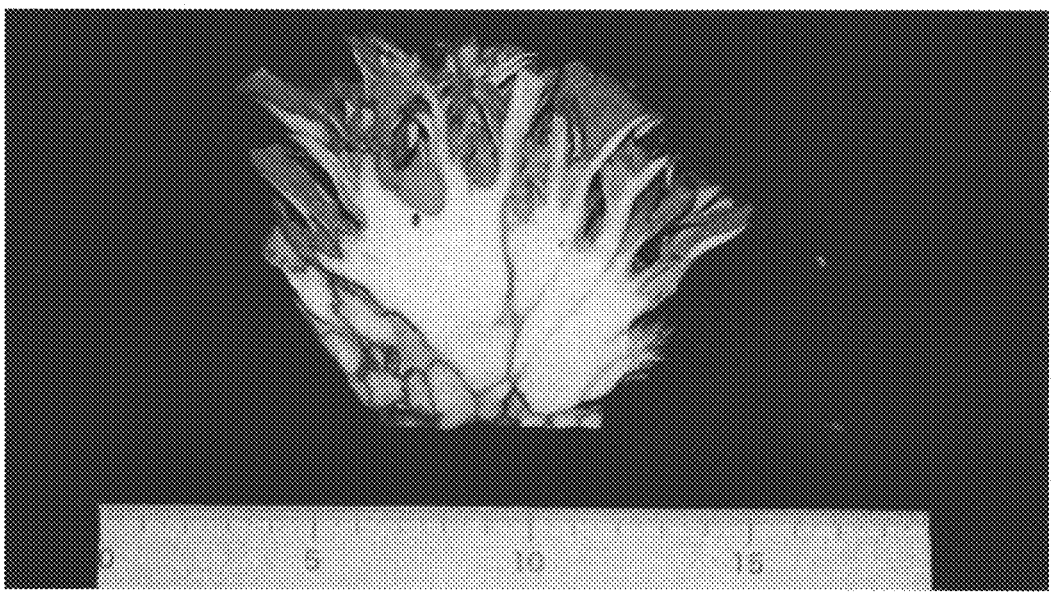
FIG. 9 is a photograph showing cross sectional view of a representative strain of MORI M51GO.

FIGS. 4 to 6 are photographs showing top view of representative strains of YUKIGUNIMAI 14GO, MORI M60GO and MORI M51GO, respectively. FIGS. 7 to 9 are photographs showing cross sectional view of representative strains of YUKIGUNIMAI 14GO, MORI M60GO and MORI M51GO, respectively.

Figure 18:
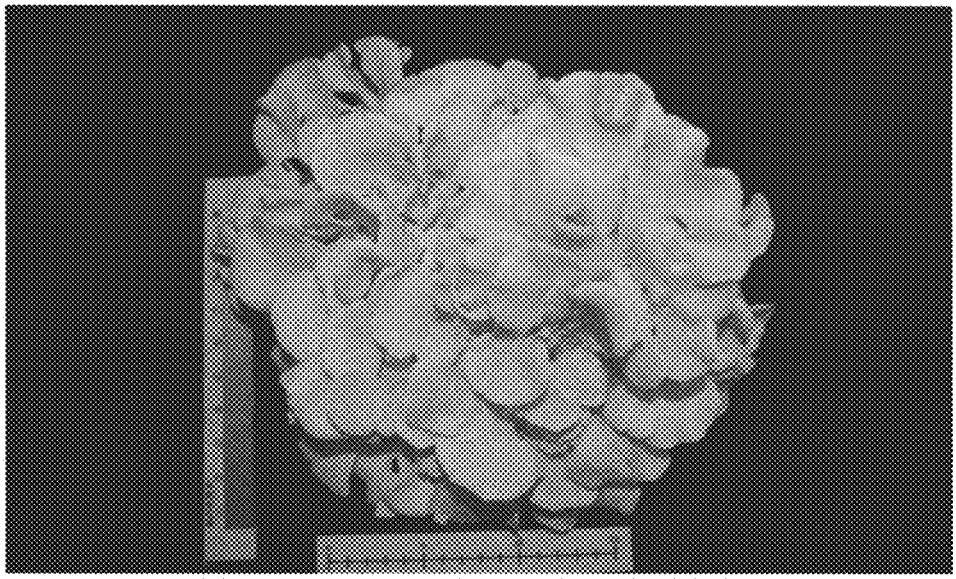
FIG. 18 is a photograph showing top view of a representative strain of YUKIGUNIMAI 14GO.
Figure 19:
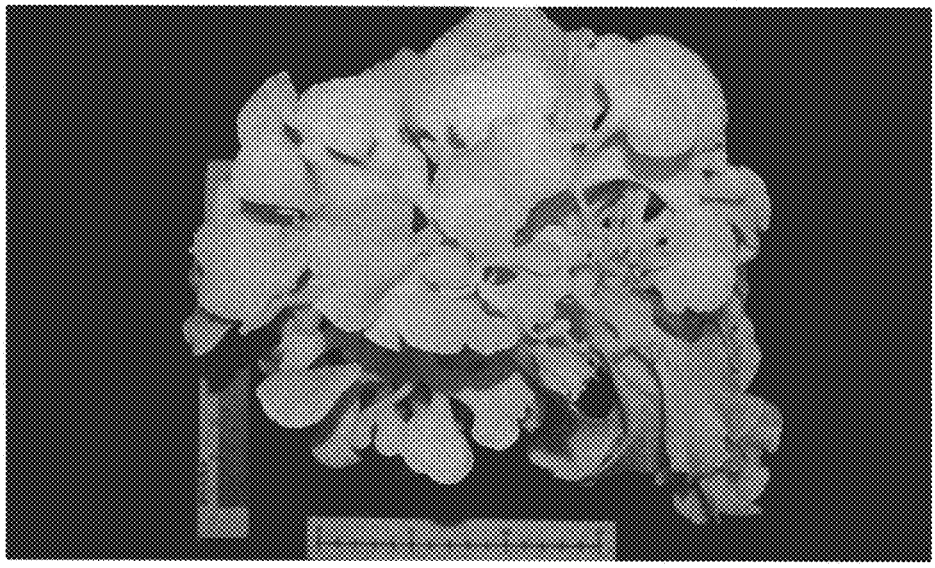
FIG. 19 is a photograph showing top view of a representative strain of AYM86.
Figure 20:
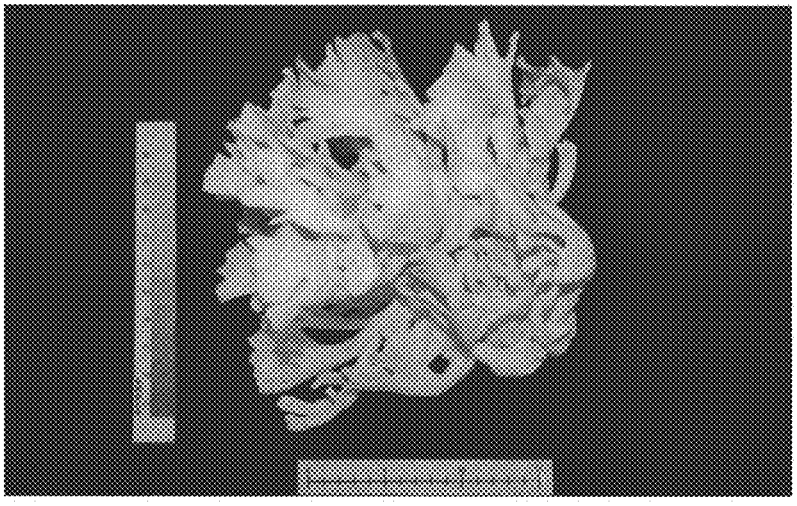
FIG. 20 is a photograph showing top view of a representative strain of C3843W.

FIGS. 18 to 20 are photographs showing top view of representative strains of YUKIGUNIMAI 14GO, AYM86 and C3843W, respectively. In terms of fruit body morphology, YUKIGUNIMAI 14GO had fewer notches in the cap periphery than AYM86. While in C3843W, some caps were spine, some are flabellate, and the vertical-sectional shape of the cap varied from upward to downward, in YUKIGUNIMAI 14GO, caps were mostly flabellate with horizontal to downward 45° C.

C. OTHER CHARACTERISTICS

YUKIGUNIMAI 14GO has a characteristic that the caps do not color after white light and/or ultraviolet light irradiation. The characteristic that the caps do not color after white light irradiation can be determined by culturing with irradiation of white light (natural light or artificial illumination) containing an ultraviolet region for at least 12 hours, preferably 72 hours, for example, 1 to 15 hours per day, preferably 2 to 12 hours per day at the time of development of the fruit body, and determining whether or not the caps of the obtained fruit body is colored. In addition, the characteristic that the caps do not color after ultraviolet irradiation can be determined by culturing with irradiation of ultraviolet light of about 0.05 to 0.2 mW/cm$^2$ for at least 7 hours, preferably 42 hours, for example, 1 to 10 hours per day, preferably 2 to 8 hours per day at the time of development of the fruit body, and determining whether or not the caps of the obtained fruit body is colored. The presence or absence of coloring can be conventionally determined by a person skilled in the art, but the presence or absence of coloring can be determined by comparison with a known variety which is known to be colored, for example. The caps of YUKIGUNIMAI 14GO are not colored after white light irradiation, and is not colored even after ultraviolet light irradiation.

Experiment 3 was conducted as follows. Specifically, YUKIGUNIMAI 14GO and MORI M60GO, and four commercially available varieties (the same as shown in Table 1)

were used to develop fruit body under ultraviolet UV-A irradiation, where the cap is likely to be colored, and the stability of white caps of YUKIGUNIMAI 14GO was examined from the coloration of the caps.

Hardwood sawdust supplemented with a nutrient mixed with such as wheat bran was used as the medium. The cultivation container was a polypropylene cultivation bag with a ventilation filter, and was sterilized by autoclaving after filling the medium. After cooling, it was inoculated with sawdust inoculum, after 60 days of culture (including stimulation of primordia formation), the filter part was removed and the bag was transferred to the development room with temperature of about 17-20° C. and humidity of 80% RH or more to stimulate development to fruit body.

Figure 10:
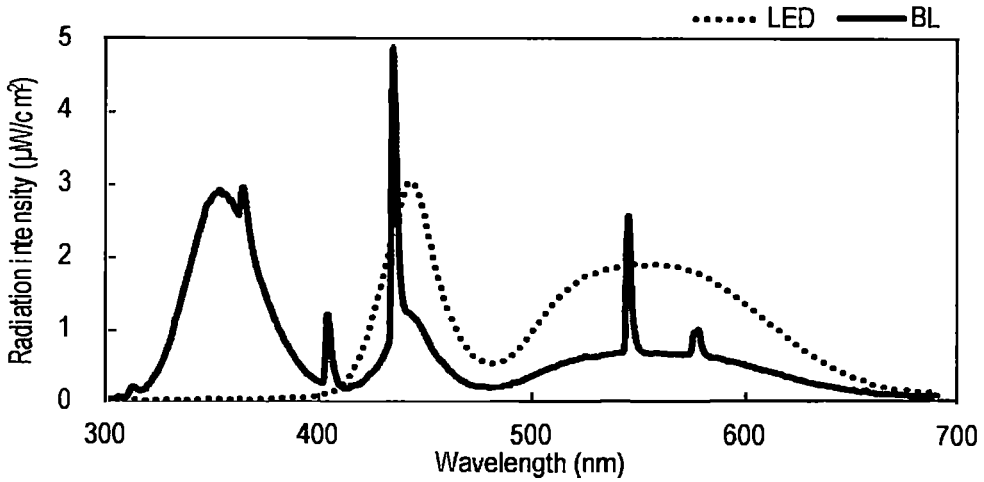
FIG. 10 is a graph showing the wavelength distribution of LED and black light (BL) used in Experiment 3.
Figure 11:
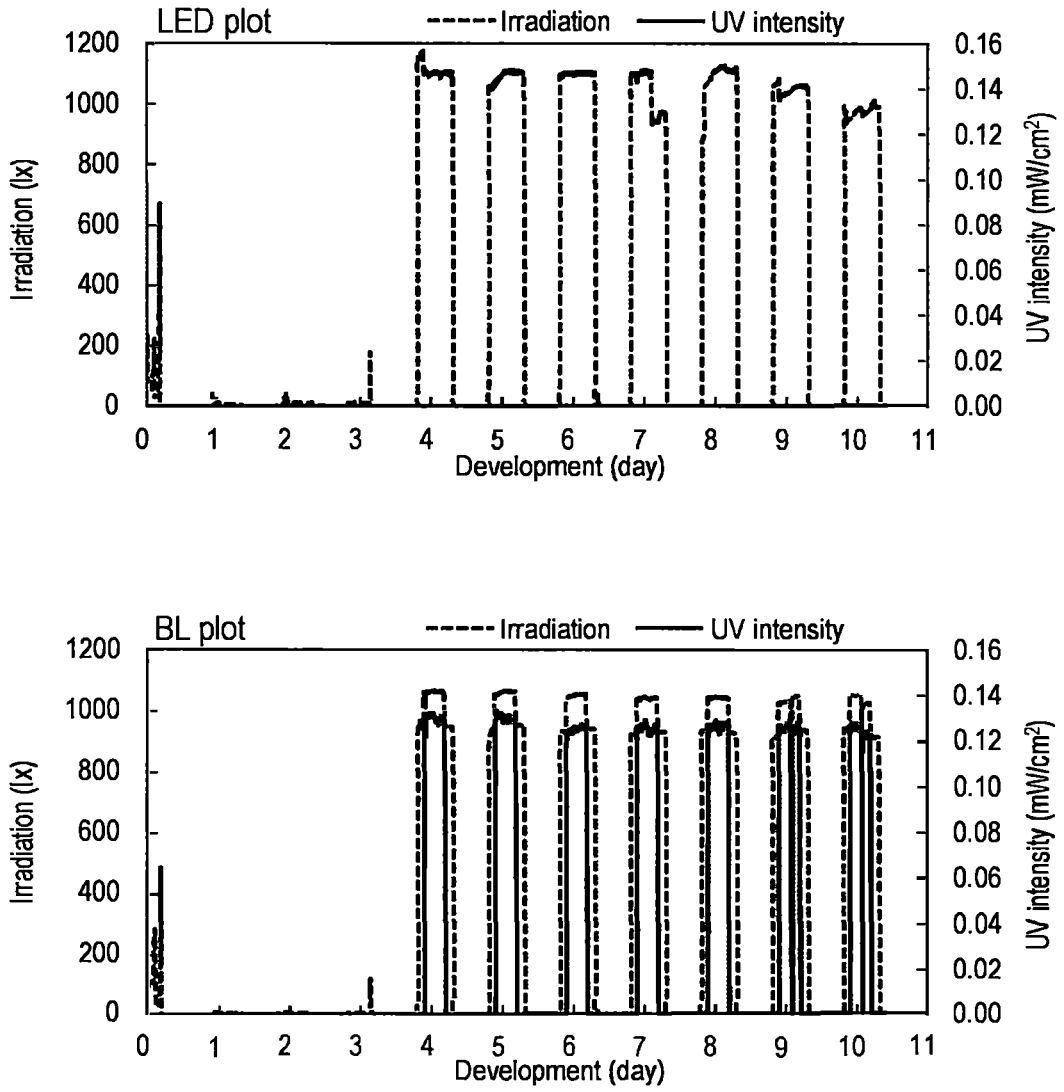
FIG. 11 is a graph showing the irradiation time and intensity of LED and black light (BL) used in Experiment 3.

Depending on light sources during fruit body development, a test plot (LED plot) using only white light-emitting diodes (LEDs) and a test plot (BL plot) combining LEDs and black lights emitting ultraviolet UV-A (HotaluX FL40SBL, hereafter, BL) were established. The wavelength distribution of each light source is shown in FIG. 10. The wavelength distribution was determined by measuring the radiation intensity ($\mu W/cm^2$) of the light source at the height of the top of the medium at 0.5 nm intervals at wavelengths of 300-700 nm using spectroradiometer PS-200 (Apogee instruments). Irradiation was started from the fourth day of development, and LED-plots were irradiated for 12 H/day (7:00-19:00). On the other hand, BL plots received 7 H/day (9:00-16:00) BL in addition to LED for 12 H/day (7:00-19:00). The irradiance at LED irradiation was more than 950 lux at the top of the medium, and the UV intensity at BL irradiation was 0.10 to 0.13 $mW/cm^2$ at the top of the medium (see FIG. 11). Irradiation and UV intensity were measured by TandD TR-74Ui (Sensor: ISA-3151).

The condition in which the developed fruit body grew sufficiently and the pores on the back of caps formed to about 2-3 mm from the edge was set as the harvest suitable period, and the color of the caps on the harvested fruit body was identified according to The R.H.S. Colour Charts. Table 5 shows the number of Colour Charts number according to The R.H.S. Colour Charts. Caps colored as GREYED-WHITE GROUP or GREY-BROWN GROUP were considered as colored caps, and the proportion of the number of fruit body in which colored caps were observed to the total number of fruit body was used as the incidence of colored caps (incidence of colored caps=number of fruit body in which colored caps were present/number of all harvested fruit body×100). This cultivation test was conducted using three bags in one test plot.

TABLE 5

Colour Charts number and abbreviated number according to the RHS Colour Charts

| Abbreviated number | RHS number | Color group |
|---|---|---|
| 1 | NN155B | WHITE |
| 2 | NN155A | GROUP |
| 3 | 156D | GREYED- |
| 4 | 156C | WHITE |
| 5 | 156B | GROUP |
| 6 | 156A | |
| 7 | 199D | GREY- |
| 8 | 199C | BROWN |
| 9 | 199B | GROUP |
| 10 | 199A | |

Figure 12A:
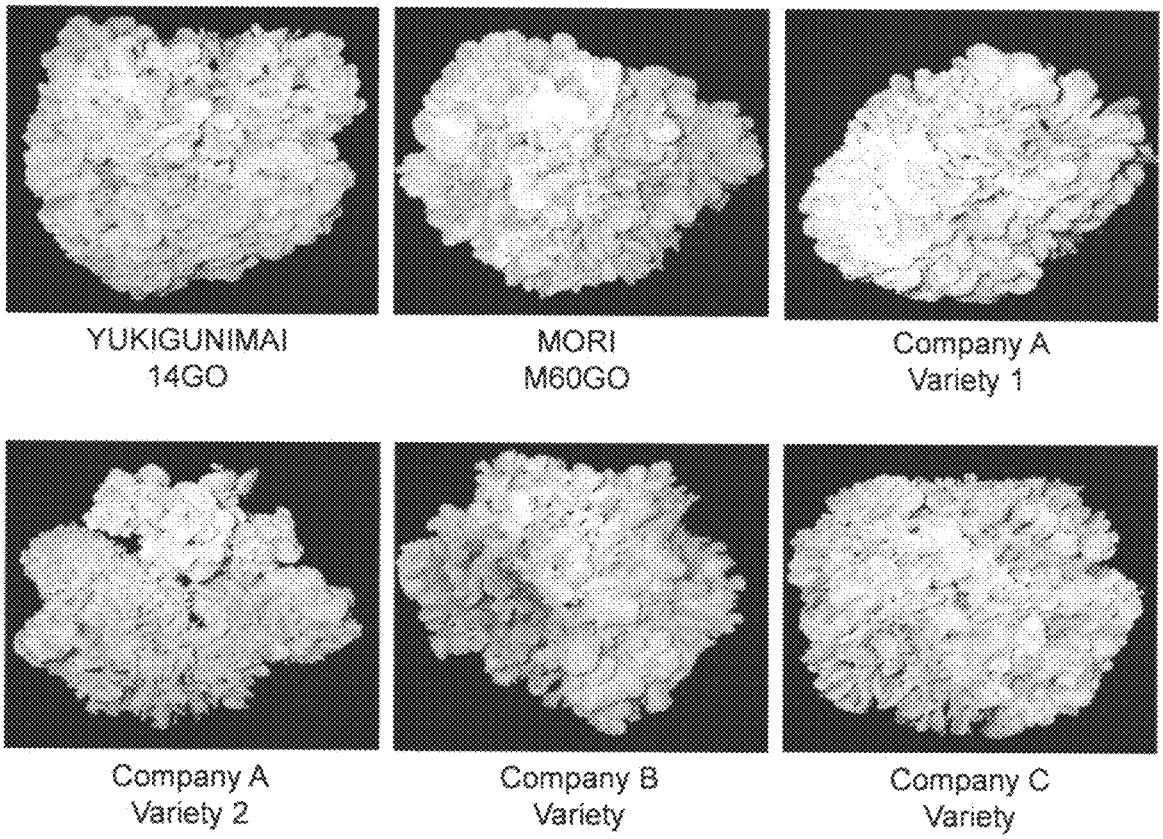
FIG. 12A illustrates photographs showing top view of representative strains in LED plots of Experiment 3.
Figure 12B:
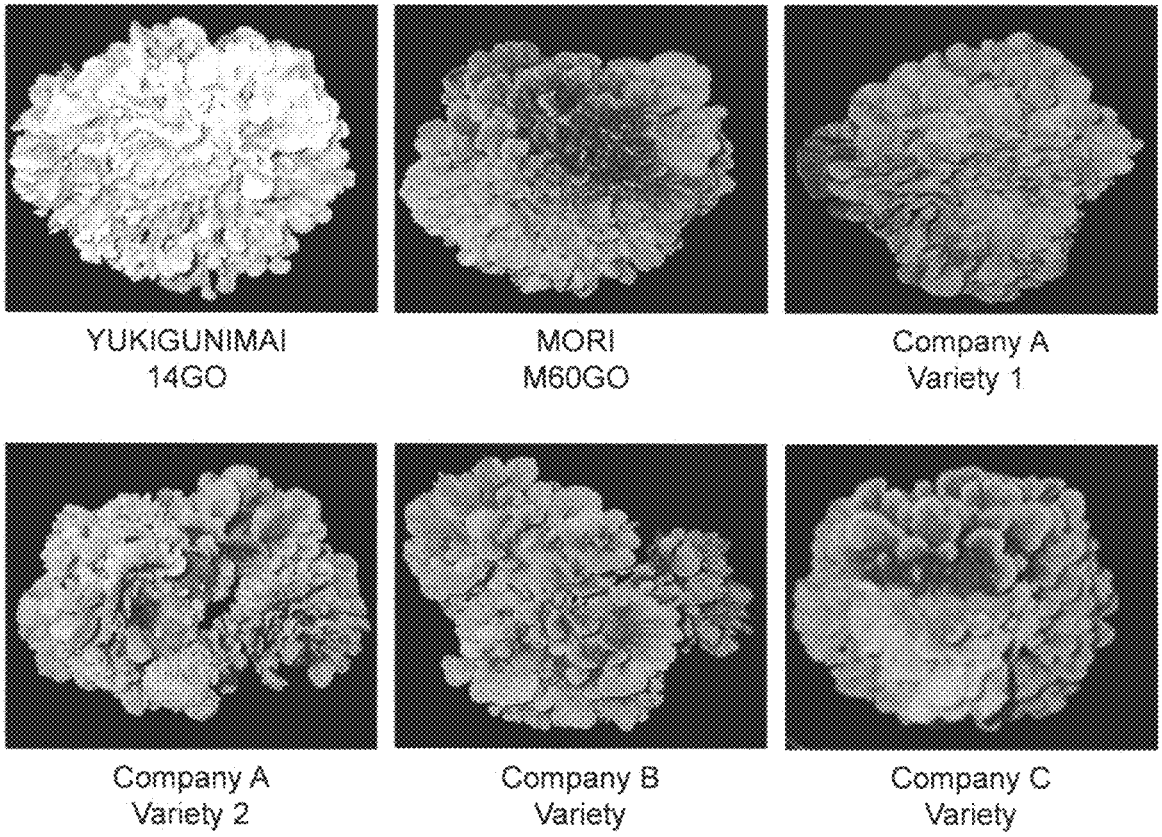
FIG. 12B illustrates photographs showing top view of representative strains in BL plots of Experiment 3.
Figure 13:
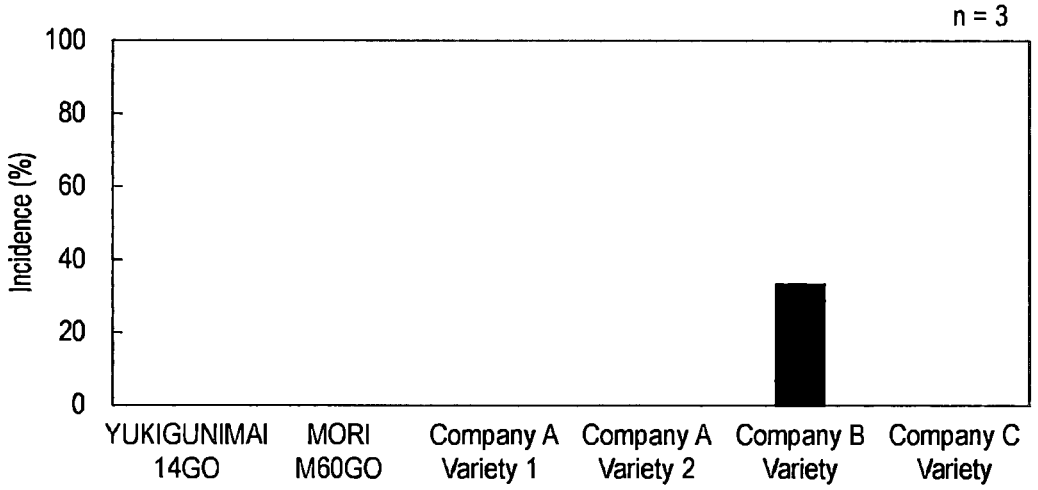
FIG. 13 is a graph showing the incidence of colored caps in LED plots of Experiment 3.
Figure 14:
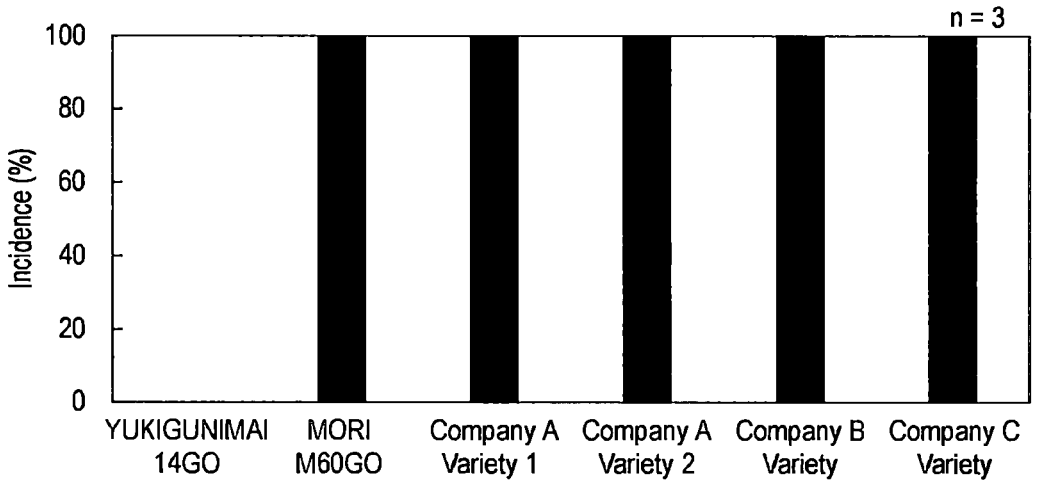
FIG. 14 is a graph showing the incidence of colored caps in BL plots of Experiment 3.

The results are shown in FIGS. 12-14. Among White Maitake varieties other than YUKIGUNIMAI 14GO, only one variety was found to be colored in the LED plots, whereas in the BL plots, the incidence of colored caps was 100% for all varieties. In contrast, YUKIGUNIMAI 14GO did not show colored caps in all fruit body in both LED-and BL-plots (0% incidence of colored caps). These results indicate that YUKIGUNIMAI 14GO is a variety with the property of producing white caps stably than the others (FIGS. 12-14).

What is claimed is:

1. A new and distinct variety of maitake mushroom plant named 'YUKIGUNIMAI 14GO' as substantially illustrated and described herein.

* * * * *